(12) United States Patent
Avinash et al.

(10) Patent No.: US 6,580,779 B2
(45) Date of Patent: Jun. 17, 2003

(54) CONTRAST ADJUSTMENT OF A DECOMPOSED X-RAY IMAGE RELATIVE TO THE CONTRAST OF ANOTHER X-RAY IMAGE

(75) Inventors: Gopal B. Avinash, New Berlin, WI (US); John M. Sabol, Sussex, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 10 days.

(21) Appl. No.: 09/989,044

(22) Filed: Nov. 20, 2001

(65) Prior Publication Data

US 2003/0095630 A1 May 22, 2003

(51) Int. Cl.$^7$ .................................................. H05G 1/64
(52) U.S. Cl. ...................... 378/98.9; 378/53; 378/98.11; 382/132
(58) Field of Search ................................ 378/5, 51, 53, 378/62, 98.8, 98.9, 98.11, 707; 382/132

(56) References Cited

U.S. PATENT DOCUMENTS

| | | | | |
|---|---|---|---|---|
| 6,052,433 A | * | 4/2000 | Chao | 378/98.9 |
| 6,343,111 B1 | * | 1/2002 | Avinash et al. | 378/98.11 |
| 6,501,819 B2 | * | 12/2002 | Unger et al. | 378/98.9 |
| 2002/0186872 A1 | * | 12/2002 | Avinash et al. | 382/132 |

* cited by examiner

*Primary Examiner*—Drew A. Dunn
(74) *Attorney, Agent, or Firm*—McAndrews, Held & Malloy, Ltd.; Peter J. Vogel; Michael A. Dellapenna

(57) ABSTRACT

An X-ray system 100 uses a display (114) to display pictures (124) generated in response to an X-ray first range of energy levels and an X-ray second range of energy levels different from the first range of energy levels. Pictures resulting from a substantially single range of X-ray energy levels also are displayed. A source (102) of X-rays transmits X-rays at the first range of energy levels through an object (106) to create in an image sensor (108) a first image and transmits X-rays at the second range of energy levels through an object to create a second image in the image sensor. A processor (110) calculates a first decomposed image from the first and second images according to a first decomposition algorithm, calculates a second decomposed image from the first and second images according to a second decomposition algorithm and calculates a contrast adjusted image in response to the first and second decomposed images. The first picture is displayed in response to the contrast adjusted image and the second picture is displayed in response to the first image.

26 Claims, 6 Drawing Sheets

CONTRAST ADJUSTMENT OF A DECOMPOSED X-RAY IMAGE RELATIVE TO THE CONTRAST OF ANOTHER X-RAY IMAGE

BACKGROUND OF THE INVENTION

The present invention relates to medical diagnostic X-ray imaging, and more specifically relates to adjustment of pictures corresponding to x-ray images.

Today, doctors and technicians commonly have access to very sophisticated medical diagnostic X-ray imaging devices. Typically during the operation of an X-ray imaging device, an X-ray source emits X-ray photons under very controlled circumstances. The X-ray photons travel through a region of interest (ROI) of a patient under examination and impinge upon a detector. In the past, X-ray imaging devices employed rudimentary film based detectors. However, recent developments have led to solid-state detectors comprised of a grid of discrete detector elements that individually respond to exposure by X-ray photons. Regardless of the detector used, however, the goal remains the same, namely to produce a clear resultant image of preselected structures of interest (e.g., specific types of tissues) within the ROI.

There is an inherent difficulty associated with producing a clear resultant image, however. In particular, because the X-ray photons travel through the entire patient, the image formed on the detector is a superposition of all the anatomic structures through which X-ray photons pass, including the preselected structures of interest. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

Attempts to reduce the effects of anatomic noise include, for example, "dual-energy" imaging. When employing dual-energy imaging, a doctor or technician acquires an image at high average X-ray photon energy, and an image at low average X-ray photon energy. Because different internal structures absorb different X-ray photon energies to different extents, it has been possible to combine the two resultant images to suppress anatomic noise according to:

$$SB(x,y) = exp[\log(H(x,y)) - w \log(L(x,y))], \quad (0 < w < 1),$$

where SB is the decomposed image achieved through the log subtraction at a specific cancellation parameter w, $H(x,y)$ is an image obtained at high energy, and $L(x,y)$ is an image obtained at low energy. By varying w, SB becomes a decomposed image of either soft tissue (i.e. soft structure) or of bone (i.e. hard structure).

Radiologists often desire to review both a standard image, which is often the original high-energy image, and the decomposed image of soft structure at the same time or in sequence. Unfortunately, the decomposed image of soft structure has a different contrast than the standard image. When the standard image and the decomposed image of soft structure are reviewed on a computer monitor, such that the user toggles back and forth between the two images, the difference in contrast may make it difficult to compare the images and to identify subtle features and differences between the images. Viewing the images in this format necessitates that the radiologist learn to read the decomposed image of soft structure differently.

The same problem is experienced when viewing the two images in other forms, such as printed on paper or film, for example. Each device (i.e. computer monitor, printer, and the like) has multiple transfer functions available, which relate pixel values to the final displayed intensity of the image. It may be possible to apply a different image transfer function to either the standard image or the decomposed image before reviewing the images in an effort to more closely match the contrast levels. However, this process is time consuming and may require the user to apply a number of different image transfer functions in a trial and error process to achieve an acceptable contrast for both images. Additionally, printing devices may require some manual manipulation to adjust the contrast of the two images, resulting in additional processing time and cost. Thus, a need has long existed in the industry for a method for adjusting the contrast of decomposed images compared to the contrast of a standard image that addresses the problems noted above and previously experienced.

BRIEF SUMMARY OF THE INVENTION

One method embodiment of the invention is useful in an X-ray system arranged to display a first picture of an object generated in response to an X-ray first range of energy levels and an X-ray second range of energy levels different from the first range of energy levels and arranged to display a second picture of the object generated in response to substantially a single range of X-ray energy levels. In such an environment, a contrast level of the first picture is adjusted relative to a contrast level of the second picture by transmitting X-rays at the first range of energy levels and second range of energy levels to generate a first image representing the object in response to the first range of energy levels and to generate a second image representing the object in response to the second range of energy levels. A first decomposed image is obtained from the first and second images according to a first decomposition algorithm, and a second decomposed image is obtained from the first and second images according to a second decomposition algorithm. A contrast-adjusted image is calculated in response to the first and second decomposed images. The first picture is displayed in response to the contrast-adjusted image, and the second picture also is displayed.

One apparatus embodiment of the invention also is useful in an X-ray system arranged to display a first picture of an object generated in response to an X-ray first range of energy levels and an X-ray second range of energy levels different from the first range of energy levels and arranged to display a second picture of the object generated in response to substantially a single range of X-ray energy level. In such an environment, a contrast level of the first picture is adjusted relative to a contrast level of the second picture by providing a source of the X-rays at the first and second ranges of energy levels. An image sensor is arranged to generate a first image representing the object in response to X-rays at the first range of energy levels and to generate a second image representing the object in response to X-rays at the second range of energy levels. A processor is arranged to calculate a first decomposed image from the first and second images according to a first decomposition algorithm, calculate a second decomposed image from the first and second images according to a second decomposition algorithm and calculate a contrast adjusted image in response to the first and second decomposed images. A display is arranged to display the first picture in response to the contrast-adjusted image and to display the second picture.

By using the foregoing techniques, X-ray pictures may be contrast adjusted with a degree of accuracy and ease previously unattainable. Such adjustment makes the pictures easier to use and decreases the amount of training required before the pictures can be accurately interpreted.

The foregoing summary, as well as the following detailed description of the embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Figure 1:
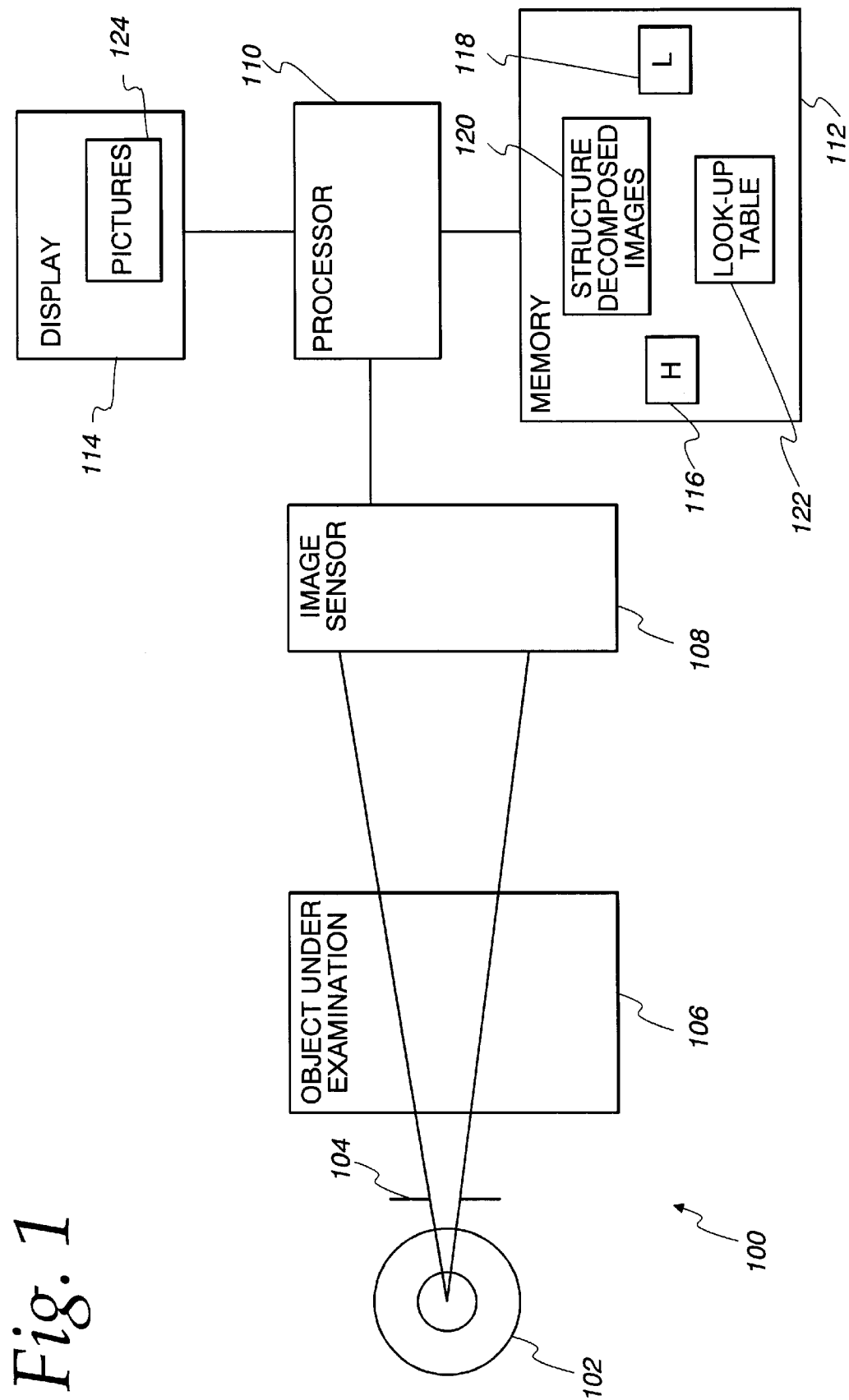
FIG. 1 is a schematic block diagram of an X-ray imaging system in accordance with a preferred embodiment of the present invention, including a memory.

FIG. 1 illustrates an X-ray imaging system 100 comprising an X-ray source 102 and a collimator 104 which subject an object 106 under examination to X-ray photons. By way of example, the X-ray source 102 may be an X-ray tube, and the object 106 under examination may be a human patient, animal, test phantom or other inanimate object under test. System 100 is useful for breast imaging, animal studies and other applications.

The X-ray imaging system 100 also includes an image sensor 108, such as a flat panel solid-state detector, coupled to a processor 110. The processor 110 (e.g., a microcontroller, microprocessor, custom ASIC, or the like) couples to a memory 112 and a display 114 by busses. The memory 112 (e.g., including one or more of a hard disk, floppy disk, CDROM, EPROM, ROM and the like) stores various images. As used in this specification and claims, image means a spatial distribution of signals suitable for representing at least one structural characteristic of an object, such as bone in a body. Examples of images are the signals stored in sensor 108 in response to X-rays and the signals stored in memory 112 corresponding to images 116 and 118. A high energy level image (H) 116 results from transmission of X-rays in the 110–140 kVp range of energy levels from source 102 through the object 106 to sensor 108. A low energy level image (L) 118 results from transmission of X-rays in the 60–90 kVp range of energy levels from source 102 through object 106 to sensor 108. The memory 112 also stores instructions for execution and a look-up table (LUT) 122 of parameters used by the processor 110, as explained below, to decompose certain types of structure in the images 116 and 118, such as hard structure (bone) or soft structure (tissue). One or more structure decomposed images 120 are thereby produced for display as pictures 124 by display 114.

The processor 110 uses decomposition algorithms to decompose spatially registered images from the structure of object 106 under examination into constituent materials (e.g., bone and soft tissue in chest X-ray images). For example, a chest X-ray image may be decomposed to create one image representing hard structure, such as bone, and one image representing soft structure, such as lung. In one embodiment, the decomposed images may be calculated using the following algorithms:

$$I_s = \frac{H}{L^{w_s}}, \qquad \text{Equation 1}$$

$$I_b = \frac{H}{L^{w_b}}, \qquad \text{Equation 2}$$

where $0 < w_s < w_b < 1$, $I_s$ is the soft structure image, $I_b$ is the hard structure image, H is the high energy level image 116, L is the low energy level image 118, $w_s$ is the decomposing parameter most likely to decompose hard structure, and $w_b$ is the decomposing parameter most likely to decompose soft structure. The decomposing parameters $w_s$ and $w_b$ are derived from the LUT 122. The soft structure image ($I_s$) and the hard structure image ($I_b$) are calculated pixel by pixel similar to the log subtraction equation.

The high energy level image (H) 116 may also be known as a standard image. The high energy level image (H) 116 and the soft structure image ($I_s$) are often viewed at the same time on the display 114 and would have the same image transfer function applied. The transfer function is the map that relates the pixel values to the final displayed intensity. The contrast of the picture resulting from the soft structure image ($I_s$) is different from the contrast of the picture resulting from the high energy level image (H) 116, thus making comparison of the two pictures difficult.

The applicants have discovered a preferred technique of adjusting the contrast of a picture resulting from the soft structure image ($I_s$) to more closely match the contrast of another X-ray picture, such as a picture resulting from the standard image (H) 116, by computing a contrast adjusted image from ($I_s$) and ($I_b$). In order to illustrate the efficacy of one form of the contrast adjusted image, as expressed in equation 5, the following proof is presented:

The following relationship is obtained by solving for the high energy level image (H) 116 in terms of $I_s$, $I_b$, $w_b$ and $w_s$:

$$H = I_s^{\frac{w_b}{w_b - w_s}} I_b^{\frac{-w_s}{w_b - w_s}} \qquad \text{Equation 3}$$

The relationship indicates that the decomposed images $I_s$ and $I_b$ are related to the standard image (H) 116 by multiplication.

By differentiation of the logarithm of Equation 3, the following contrast equation is derived:

$$C(H) = \frac{w_b}{w_b - w_s} C(I_s) - \frac{w_s}{w_b - w_s} C(I_b), \qquad \text{Equation 4}$$

where C(H) is the contrast of the high energy image (H) 116, C($I_s$) is the contrast of the soft structure image ($I_s$), and C($I_b$) is the contrast of the hard structure image ($I_b$).

From Equation 4, it can be shown that a contrast adjusted soft-tissue image ($I_{HS}$) can be obtained using the following contrast matching algorithm:

$$I_{HS} = I_s^{\frac{w_b}{w_b-w_s}} LPF\left(I_b^{\frac{-w_s}{w_b-w_s}}\right).  \quad \text{Equation 5}$$

wherein $w_b/w_b-w_s$ and $-w_s/w_b-w_s$ are exponents and wherein the function LPF performs a low-pass filtering function.

Several low-pass functions can be used for this purpose. A boxcar filtering function is recommended because of its computational efficiency. A boxcar filter smoothes an image by the average of a given neighborhood. It is separable and efficient methods exist for its computation. Each point in the image requires just four arithmetic operations, irrespective of the kernel size. The length of the separable kernel is variable but a preferred value is 125 for a 1024×1024 image.

Figure 2:
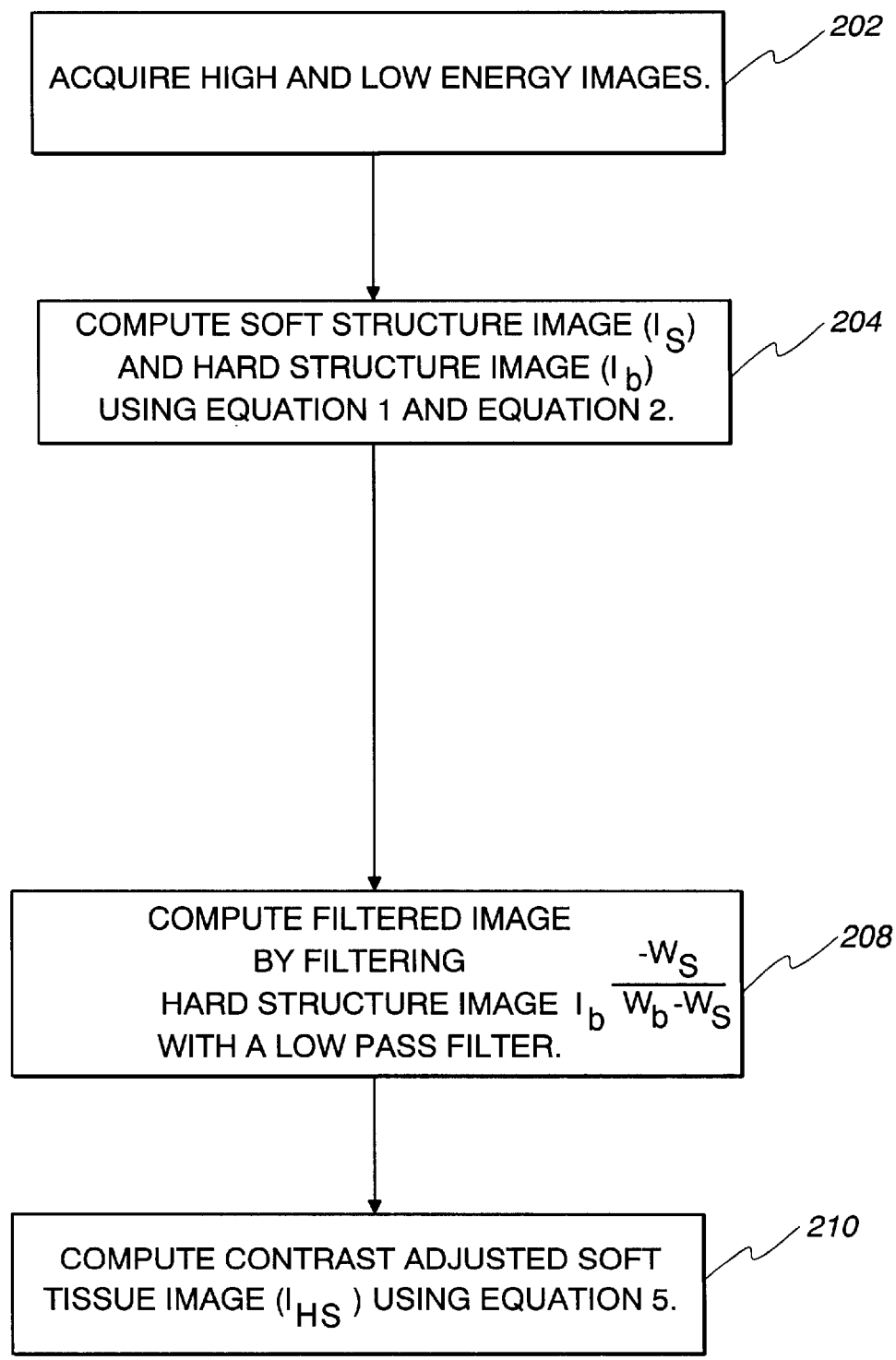
FIG. 2 is a flow chart illustrating a process for creating a contrast-adjusted image in accordance with a preferred embodiment of the present invention.

FIG. 2 illustrates a process to create a preferred form of contrast adjusted image in accordance with the present invention. At Step 202, a high energy level image (H) 116 and a low energy level image (L) 118 are acquired and stored in memory 112. The images 116 and 118 contain representations of both hard and soft structure. Acquisition of the high and low energy level images may be achieved by the structure shown in FIG. 1 or by a computed radiography dual-energy system that transmits a dual energy beam which is used to record a low energy image on a first plate and a high energy image on a second plate. A filter typically separates the first and second plates.

At Step 204, a hard structure image ($I_b$) and a soft structure image ($I_s$) are calculated. The processor 110 determines a decomposing parameter that is likely to decompose hard structure ($w_s$) and a decomposing parameter that is likely to decompose soft structure ($w_b$). In an embodiment of the present invention, the decomposing parameters $w_s$ and $w_b$ are derived from the LUT 122. The LUT 122 contains decomposing parameters having a range of values based on humanoid phantom studies or on human patients corresponding to different kVp level values for high energy level images (H) 116 and low energy level images (L) 118. The appropriate decomposing parameter is selected by processor 110 depending on the value of the energy level of the X-ray transmitted through object 106. The decomposed images may be calculated using Equation 1 and Equation 2, or the log subtraction equation as explained previously.

Before lowpass filtering, the hard structure image ($I_b$) is mirrored in the positive and negative horizontal directions, and in the positive and negative vertical directions. By mirroring the hard structure image ($I_b$), the hard structure image ($I_b$) is expanded.

Figure 3:
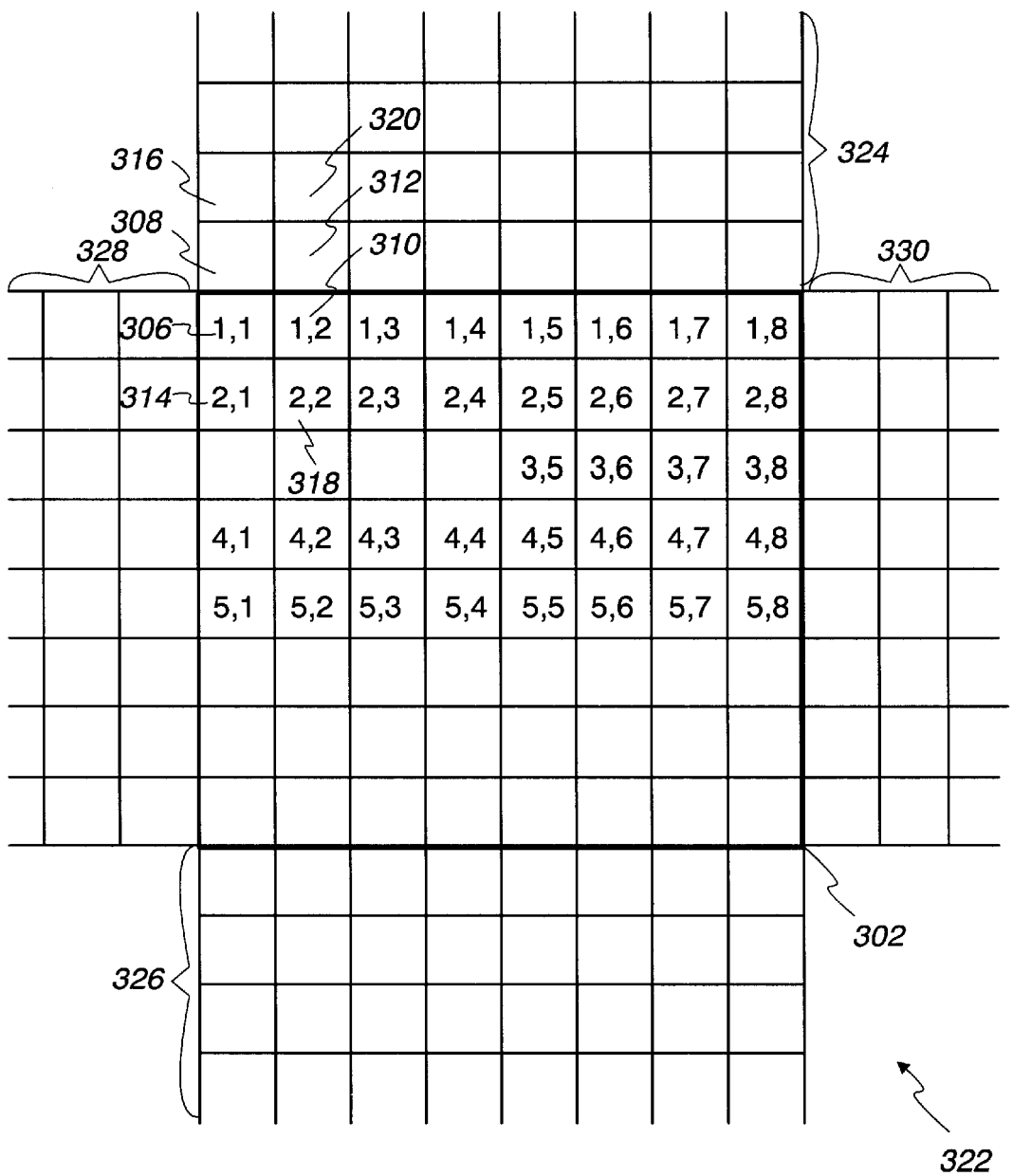
FIG. 3 is a schematic block diagram illustrating a portion of the memory shown in FIG. 1 and illustrating a method of expanding an image in accordance with an embodiment of the present invention.
Figure 3:
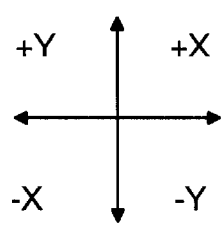

FIG. 3 illustrates a method of expanding an image in accordance with an embodiment of the present invention. Expanded image 322 comprises image 302 stored at corresponding memory locations, which may be the hard structure image ($I_b$), and additional pixels stored in the memory locations 324, 326, 328 and 330 that temporarily hold mirrored pixel data. Image 302 comprises multiple pixels 306, 310, 314, and 318 arranged in rows and columns. Memory location 324 stores pixels that hold the mirrored pixel data from the image 302, including pixels 308, 312, 316, and 320. In FIG. 3, pixels are identified by row and column separated by a comma. For example, the pixel 2,1 is located in row 2 of column 1.

The image 302 needs to be expanded so that an image filter may process the pixels in the edge rows and columns. The number of rows and columns to be mirrored is determined by the requirements of the image filter. The image filter is discussed below.

To mirror the image 302 in the positive vertical direction (+Y), the values of the pixels are copied such that the value of pixel (1,1) 306 is copied to pixel location 308 and the value of pixel (1,2) 310 is copied to pixel location 312. Pixels 308 and 312 are located in memory location 324. This process is repeated until all pixels in the first row have been copied. The process then continues to the second row, such that the value of pixel (2,1) 314 is copied to pixel location 316 and the value of pixel (2,2) 318 is copied to pixel location 320. This process is repeated for the positive (+Y) and negative vertical direction (-Y), and the positive (+X) and negative horizontal directions (-X), copying the number of rows and columns required by the image filter to produce the expanded image 322.

Referring to FIG. 2, in Step 208, a preliminary filtered image is computed by filtering an expanded hard structure image $I_b$ with a low pass filter. Each pixel in the hard structure image ($I_b$) is modified by the decomposing parameters as illustrated by Equation 5. A boxcar filter, or other low-pass image filter, is utilized to compute the filtered image. The final filtered image is obtained by retaining the filtered image at the original unexpanded image 302.

Figure 4:
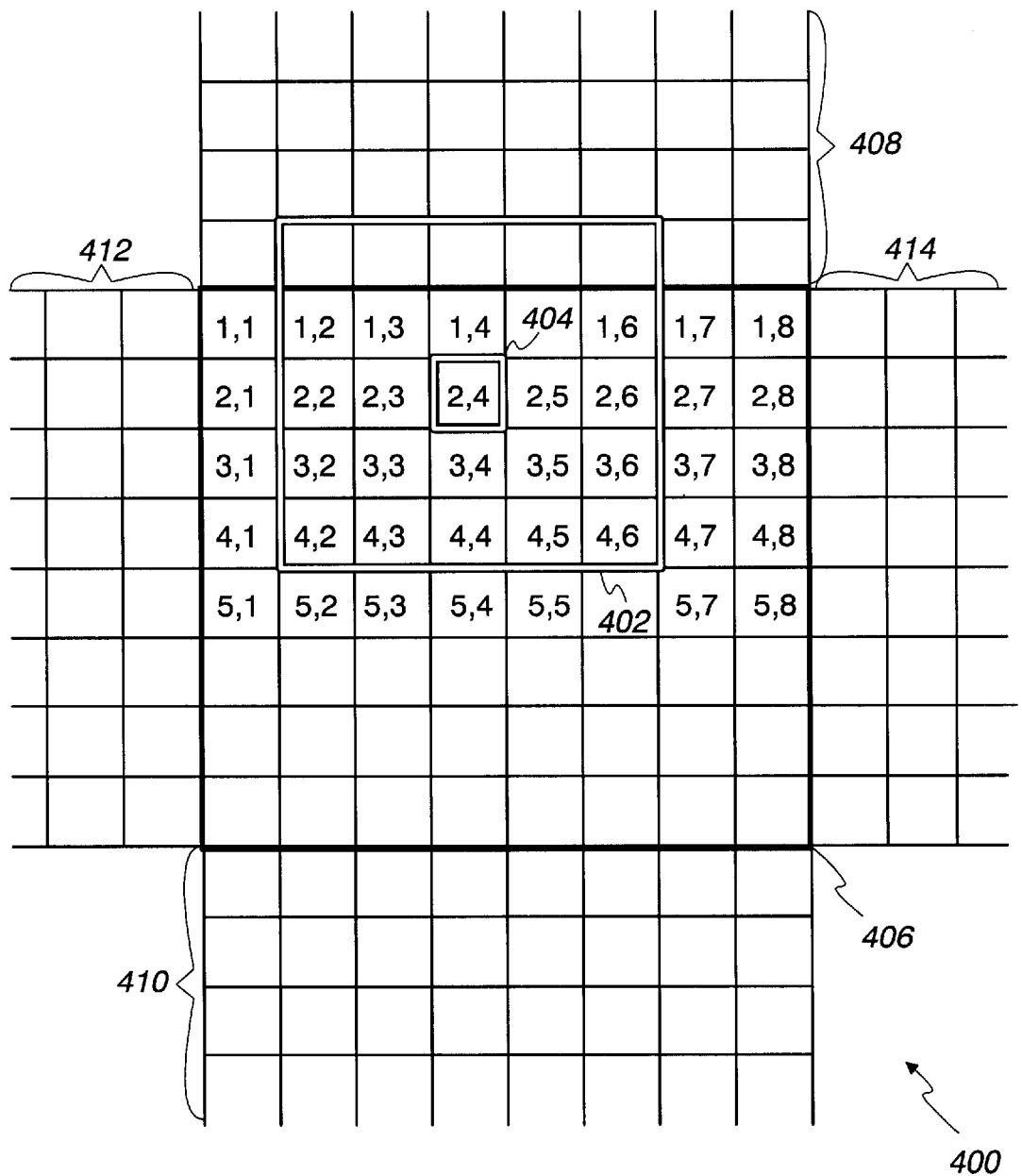
FIG. 4 is a schematic block diagram illustrating a portion of the memory shown in FIG. 1 and illustrating a moving average method of computing a filtered image utilizing a boxcar filter in accordance with an embodiment of the present invention.

FIG. 4 illustrates a moving average method of computing a filtered image utilizing a boxcar filter in accordance with an embodiment of the present invention. FIG. 4 includes expanded image 400, stored in memory locations 408, 410, 412, and 414 as previously discussed, and image 406. The expanded image 400 is the hard structure image $I_b$ and the memory locations 324, 326, 328, and 330 that have been modified by the decomposing parameters (i.e., $w_s$ and $w_b$) illustrated by Equation 5. In the moving average method, all pixel values within a defined kernel (e.g. a "box" 402) around a central pixel 404, which is a pixel located at the center of the box 402, are averaged together to compute the pixel values of the filtered image. The filtered image contains the same number of pixel locations as image 406.

The moving average method utilizes a box 402 that is square. For example, the box 402 is 5 pixels by 5 pixels in size and is centered on the center pixel 404, which is located at row 2, column 4 (2,4). The box 402, when centered on the center pixel 404, includes pixel locations in memory location 324 that hold mirrored pixel values as previously discussed. The box 402 may contain any number of pixels defined by the boxcar filter. The value of every pixel located inside the box 402 is read by the processor 110 and added together to compute a total pixel value. The average pixel value is determined by dividing the total pixel value by the number of pixels inside the box 402. In this example, there are 25 pixels inside box 402, so the average pixel value is computed by dividing the total pixel value by 25. The average pixel value is stored at pixel location (2,4) of the filtered image.

The box 402 is then moved so that the center pixel 404 is located at row 2, column 5 (2,5). The processor 110 reads the value of every pixel located inside the box 402, and the average pixel value is determined. The average pixel value is stored at pixel location (2,5) of the filtered image. This process is repeated for every pixel location in image 406.

Figure 5:
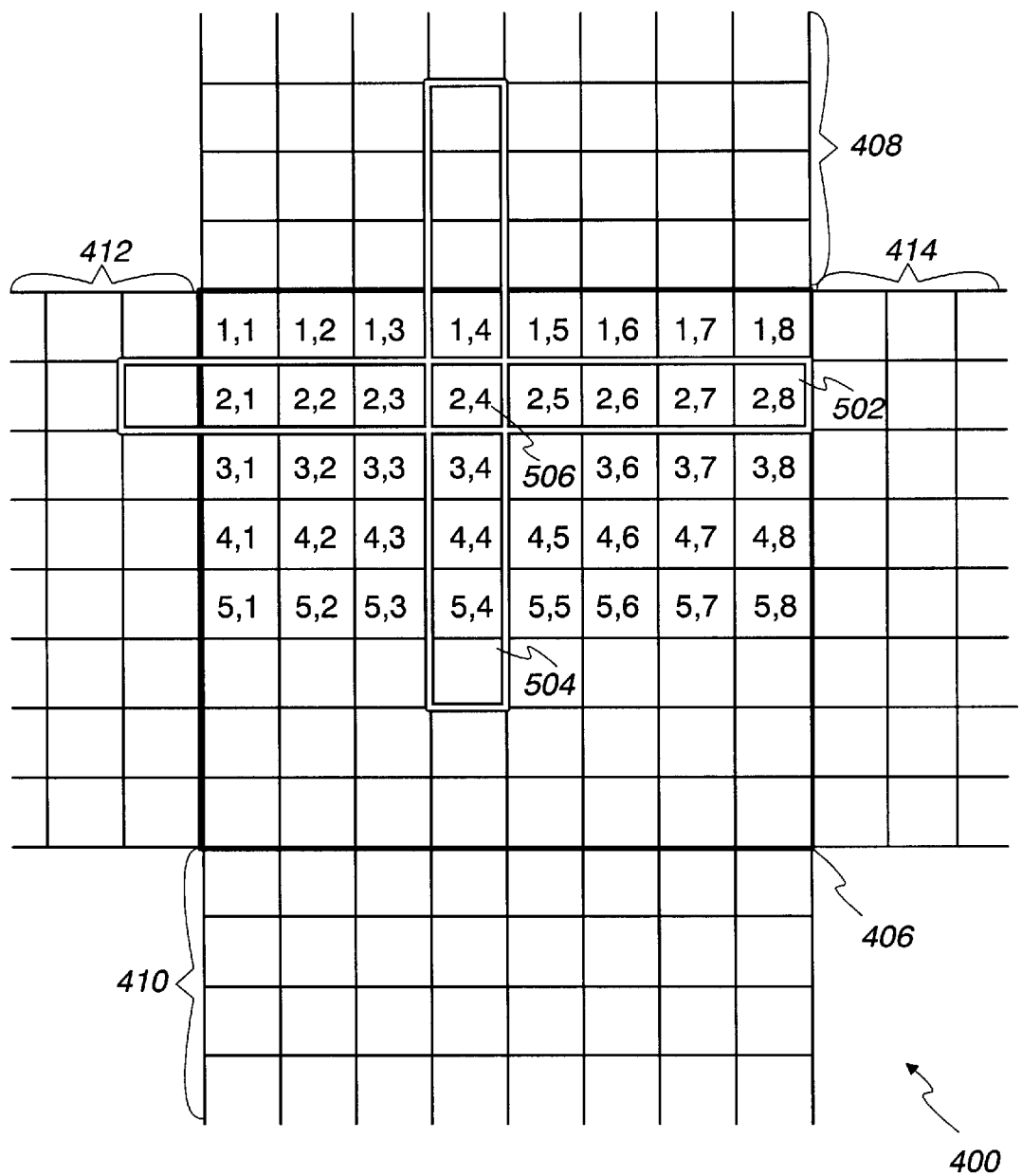
FIG. 5 is a schematic block diagram illustrating a portion of the memory shown in FIG. 1 and illustrating a separable method of computing a filtered image utilizing a boxcar filter in accordance with an embodiment of the present invention.
Figure 5:
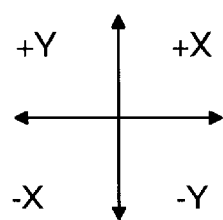

FIG. 5 illustrates a separable method of computing a filtered image utilizing a boxcar filter in accordance with an embodiment of the present invention. FIG. 5 includes the expanded image 400, comprising image 406 and values stored in memory locations 408, 410, 412, and 414 as previously discussed. The separable method utilizes rectangular boxes 502 and 504 around a central pixel 506, which is located at the center of box 502, and box 504. The separable method creates an intermediate image and a filtered image. As with the moving average boxcar method of FIG. 4, the filtered image contains the same number of pixel locations as image 406.

Averaging the pixel values inside the box 502 creates the intermediate image. The box 502 is a rectangle and lies in the horizontal direction. For example, the box 502 is 1 pixel by 9 pixels in size, is centered on the center pixel 506, and lies along row 2. The center pixel 506 is located at row 2, column 4 (2,4). One value from memory location 412 is utilized to calculate the value of the pixel (2,4) of the intermediate image. The boxes 502 and 504 may contain any number of pixels defined by the boxcar filter, but boxes 502 and 504 will each contain the same number of pixels. The values of all the pixels located inside the box 502 are read and averaged by the processor 110 to compute the value of the pixel (2,4) of the intermediate image. This process is repeated for every pixel location in image 406. The pixel values stored in the memory locations 408 and 410 are copied to the intermediate image.

Next, the filtered image is created by averaging the pixel values of the intermediate image in the vertical direction. The box 504 is a rectangle 1 pixel by 9 pixels in size, and lies in the vertical direction. Continuing with the above example, the box 504 is centered on the center pixel 506 (2,4) and lies along column 4. Three pixel values in memory location 408 are included in box 504. The values of all the pixels located inside the box 504 are read and averaged by the processor 110 to compute the value of the pixel (2,4) of the filtered image. This process is repeated for every pixel location in the intermediate image.

Figure 6:
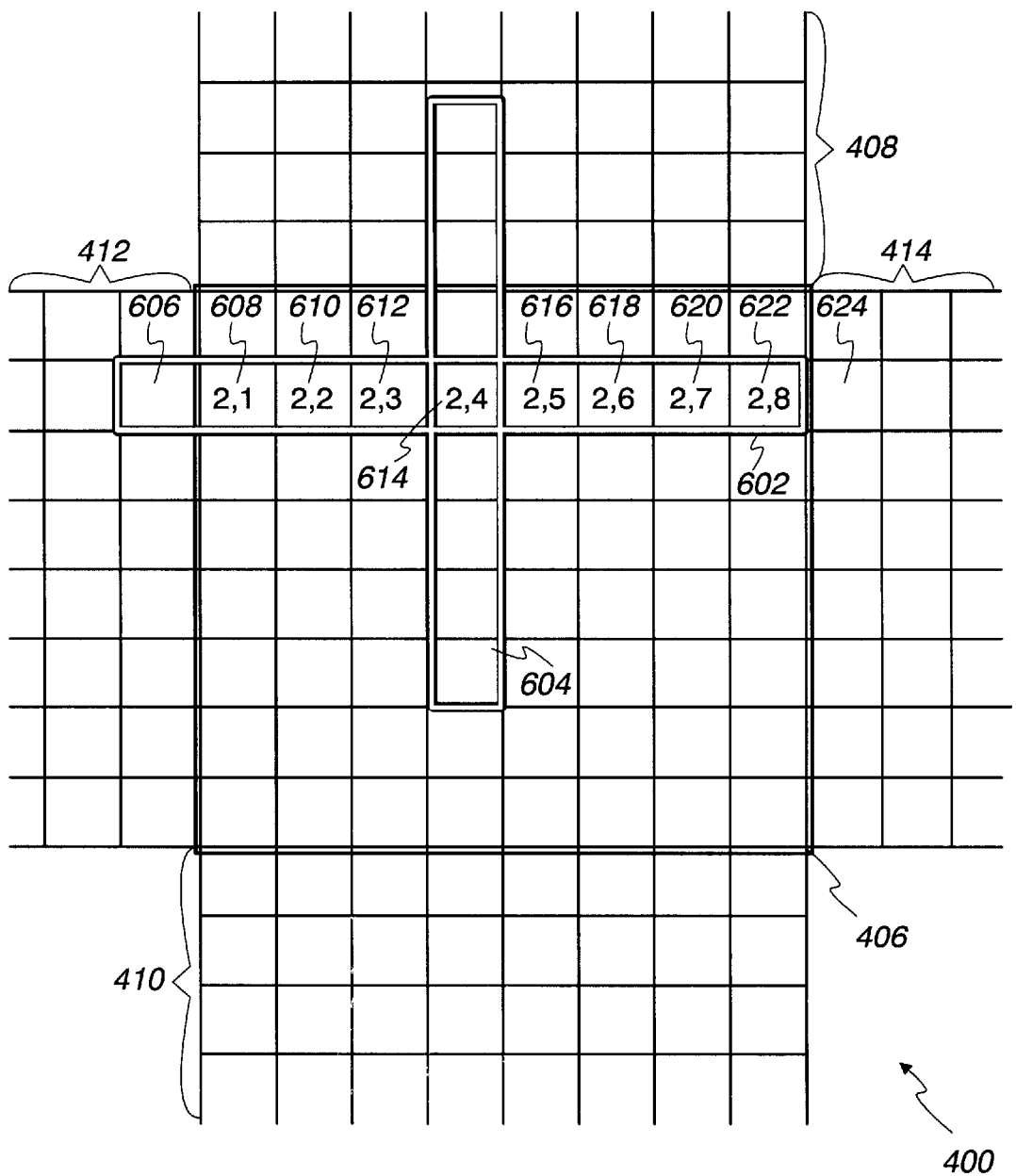
FIG. 6 is a schematic block diagram illustrating a portion of the memory shown in FIG. 1 and illustrating an additional separable method of computing a filtered image utilizing a boxcar filter in accordance with an embodiment of the present invention.
Figure 6:
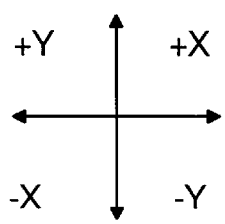

FIG. 6 illustrates an additional separable method of computing a filtered image utilizing a boxcar filter in accordance with an embodiment of the present invention. FIG. 6 includes the expanded image 400, comprising image 406 and values stored in memory locations 408, 410, 412, and 414 as previously discussed. The separable method utilizes two boxes 602 and 604, and pixels 606 through 624 are illustrated. An intermediate image and a filtered image are created. The filtered image contains the same number of pixel locations as image 406.

The separable method of FIG. 6 is similar to the separable method of FIG. 5. The intermediate image is created by averaging the pixel values inside the box 602 as it is moved across the image 406. For example, the box 602 is 1 pixel by 9 pixels in size, is centered on the center pixel 614, and lies along row 2. The center pixel 614 is located at row 2, column 4 (2,4). The values of the pixels 606 through 622 are read and averaged by the processor 110 to compute the new value of the pixel (2,4) of the intermediate image.

Next, the box 602 is moved by 1 pixel value. The box 602 is now centered on center pixel 616, located at row 2, column 5 (2,5). The processor 110 retains the values of pixels 608 through 622, and discards the value of pixel 606. The value of pixel 624, now located within box 602, is read and added to the retained values of pixels 608 through 622 to compute a total value. The average of the total value is stored in the location of pixel (2,5) of the intermediate image.

This process is repeated for every pixel location in image 406. The pixel values stored in the memory locations 408 and 410 are copied to the intermediate image.

The filtered image is then created by averaging the pixel values of the intermediate image in the vertical direction, using the same process as was used to create the intermediate image. That is, the values of the pixels of the intermediate image located inside box 604 are read, averaged, and stored in the corresponding central pixel location of the filtered image. The pixel values are retained as the box 604 moves across the image 406.

The final result LPF (.) is obtained by retaining the filtered image at original pixel or memory locations corresponding to the hard structure image $I_b$ prior to expanding. For example, referring to FIG. 3, the final result LPF(.) is obtained by retaining the filtered image at original pixel or memory locations 302. Referring to FIG. 4, the final result LPF(.) is obtained by retaining the filtered image at original pixel or memory locations 402. Referring to FIGS. 5 and 6, the final result LPF(.) is obtained by retaining the filtered image at original pixel or memory locations 406.

The creation of the filtered image by the separable method of FIG. 6 is more computationally efficient than the separable method of FIG. 5 and the moving average method of FIG. 4, because the pixel values inside boxes 602 and 604 are retained. Each time the boxes 602 and 604 are moved, only one new pixel value is read before the average pixel value is determined.

In Step 210 of FIG. 2, a contrast adjusted soft tissue image ($I_{HS}$) is computed by the processor 110 utilizing the Equation 5. Equation 5 is repeated below for clarity:

$$I_{HS} = I_s^{\frac{w_b}{w_b-w_s}} LPF\left(I_b^{\frac{-w_s}{w_b-w_s}}\right).\qquad\text{Equation 5}$$

$$LPF\left(I_b^{\frac{-w_s}{w_b-w_s}}\right)$$

is the filtered image created by filtering $$I_b^{\frac{-w_s}{w_b-w_s}}$$

with a low pass filter, such as the boxcar filter of FIG. 6, as discussed previously.

The contrast level of a picture resulting from the contrast adjusted soft tissue image ($I_{HS}$) is matched to the contrast level of a picture resulting from the high energy level image (H) 116, and pictures resulting from the images $I_{HS}$ and H may now be easily compared. The pictures resulting from images $I_{HS}$ and H may be toggled back and forth on the display 114 to improve the visualization of subtle features without the user comparing pictures that have different contrast levels or requiring the user to learn to read a picture resulting from the decomposed soft tissue image ($I_s$) differently than a picture resulting from the standard image (H) 116. Additionally, it is not necessary to develop or apply different image transfer functions for the display 114 or other device in an attempt to match the contrast of pictures resulting from the standard image (H) 116 and the contrast of pictures resulting from the soft structure image ($I_S$), because images $I_{HS}$ and H have the same response to the same transfer functions.

While the invention has been described with reference to at least one embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an X-ray system arranged to display a first picture of an object generated in response to an X-ray first range of energy levels and an X-ray second range of energy levels different from the first range of energy levels and arranged to display a second picture of the object generated in response to substantially a single range of X-ray energy levels, a method for adjusting a contrast level of the first picture relative to a contrast level of the second picture comprising:

transmitting X-rays at the first range of energy levels and the second range of energy levels through the object to generate a first image representing the object in response to the first range of energy levels and to generate a second image representing the object in response to the second range of energy levels;

obtaining a first decomposed image from the first and second images according to a first decomposition algorithm;

obtaining a second decomposed image from the first and second images according to a second decomposition algorithm;

computing a contrast adjusted image in response to the first and second decomposed images;

displaying the first picture in response to the contrast adjusted image; and displaying the second picture.

2. The method of claim 1, wherein said computing comprises filtering the first decomposed image to create a filtered image and combining the filtered image with the second decomposed image to create the contrast adjusted image.

3. The method of claim 2, wherein said filtering comprises low pass filtering.

4. The method of claim 3, wherein the second picture is displayed in response to one of the first and second images.

5. The method of claim 4, wherein the object comprises at least a first type of structure and a second type of structure, wherein the first decomposition algorithm decomposes the second type of structure more than the first type of structure and wherein the second decomposition algorithm decomposes the first type of structure more than the second type of structure.

6. The method of claim 5, wherein the first type of structure comprises hard structure and the second type of structure comprises soft structure and wherein the first decomposed image comprises a hard structure image and wherein the second decomposed image comprises a soft structure image.

7. The method of claim 2, and further comprising storing the first decomposed image at a set of memory locations extending in a first direction and in a second direction perpendicular to the first direction and wherein said filtering comprises:

expanding the first decomposed image by mirroring the first decomposed image in the first and second directions to create an expanded image;

low pass filtering the expanded image to create a preliminary filtered image; and retaining the portion of the preliminary filtered image corresponding to the set of memory locations to create the filtered image.

8. The method of claim 7, wherein said low pass filtering further comprises:

creating an intermediate image by applying a separable boxcar filter function to the expanded image in the first direction; and creating the preliminary filtered image by applying the separable boxcar filter function to the intermediate image in the second direction.

9. The method of claim 8, wherein said expanded image comprises pixel values, wherein the boxcar filter function defines sets of the pixel values and wherein said applying a separable boxcar filter function to the expanded image in the first direction and said applying the separable boxcar filter function to the intermediate image in the second direction each comprises:

defining a first set of pixel values within the sets of pixel values;

calculating a first average pixel value based on the first set of pixel values;

retaining a plurality of pixel values within the first set of pixel values;

defining a second set of pixel values including the plurality of pixel values; and calculating a second average pixel value based on the second set of pixel values.

10. The method of claim 1, wherein the method further comprises storing a plurality of decomposition parameters having a predetermined range of values, wherein the first range of energy levels is selected from a first range of energy level values, wherein the second range of energy levels is selected from a second range of energy level values, wherein said obtaining a first decomposed image comprises selecting a first decomposition parameter from the plurality of decomposition parameters depending on the value of the first range of energy levels and using the first decomposition parameter to calculate the first decomposed image, and wherein said obtaining a second decomposed image comprises selecting a second decomposition parameter from the plurality of decomposition parameters depending on the value of the second range of energy levels and using the second decomposition parameter to calculate the second decomposed image.

11. The method of claim 10, wherein the object comprises hard structure and soft structure, wherein the first decomposed image comprises a hard structure image of the hard structure and wherein the second decomposed image comprises a soft structure image of the soft structure.

12. The method of claim 11, wherein said computing comprises calculating the contrast adjusted image according to the equation:

$$I_{HS} = I_s^{\frac{w_b}{w_b - w_s}} LPF\left(I_b^{\frac{-w_s}{w_b - w_s}}\right)$$

wherein $I_s$ represents the soft structure image, $I_b$ represents the hard structure image, $w_s$ represents the second selected decomposition parameter, $w_b$ represents the first selected decomposition parameter, and LPF represents a low pass filter function.

13. The method of claim 12, wherein the low pass filter function comprises a boxcar filter function.

14. In an X-ray system arranged to display a first picture of an object generated in response to an X-ray first range of energy levels and an X-ray second range of energy levels different from the first range of energy levels and arranged to display a second picture of the object generated in response to substantially a single range of X-ray energy levels, apparatus for adjusting a contrast level of the first picture relative to a contrast level of the second picture comprising:

a source of the X-rays at the first and second ranges of energy levels arranged to transmit the X-rays at the first and second ranges of energy levels through the object;

an image sensor arranged to generate a first image representing the object in response to X-rays at the first range of energy levels and to generate a second image representing the object in response to X-rays at the second range of energy levels;

a processor arranged to calculate a first decomposed image from the first and second images according to a first decomposition algorithm, calculate a second decomposed image from the first and second images according to a second decomposition algorithm and calculate a contrast adjusted image in response to the first and second decomposed images; and a display arranged to display the first picture in response to the contrast adjusted image and to display the second picture.

15. The apparatus of claim 14, wherein said processor is arranged to conduct filtering of the first decomposed image to create a filtered image and to combine the filtered image with the second decomposed image to create the contrast adjusted image.

16. The apparatus of claim 15, wherein said filtering comprises low pass filtering.

17. The apparatus of claim 16, wherein the second picture is displayed in response to one of the first and second images.

18. The apparatus of claim 17, wherein the object comprises at least a first type of structure and a second type of structure, wherein the processor uses the first decomposition algorithm to decompose the second type of structure more than the first type of structure and wherein the processor uses the second decomposition algorithm to decompose the first type of structure more than the second type of structure.

19. The apparatus of claim 18, wherein the first type of structure comprises hard structure and the second type of structure comprises soft structure and wherein the first decomposed image comprises an image of hard structure and wherein the second decomposed image comprises an image of soft structure.

20. The apparatus of claim 15, wherein the processor is arranged to store the first decomposed image at a set of memory locations extending in a first direction and in a second direction perpendicular to the first direction and wherein said filtering comprises:

expanding the first decomposed image by mirroring the first decomposed image in the first and second directions to create an expanded image;

low pass filtering the expanded image to create a preliminary filtered image; and retaining the portion of the preliminary filtered image corresponding to the set of memory locations to create the filtered image.

21. The apparatus of claim 20, wherein said low pass filtering further comprises:

creating an intermediate image by applying a separable boxcar filter function to the expanded image in the first direction; and creating the preliminary filtered image by applying the separable boxcar filter function to the intermediate image in the second direction.

22. The apparatus of claim 21, wherein said expanded image comprises pixel values, wherein the boxcar filter function defines sets of the pixel values and wherein said applying a separable boxcar filter function to the expanded image in the first direction and said applying the separable boxcar filter function to the intermediate image in the second direction each comprises:

defining a first set of pixel values within the sets of pixel values;

calculating a first average pixel value based on the first set of pixel values;

retaining a plurality of pixel values within the first set of pixel values;

defining a second set of pixel values including the plurality of pixel values; and calculating a second average pixel value based on the second set of pixel values.

23. The apparatus of claim 14, wherein the system further comprises a memory storing a plurality of decomposition parameters having a predetermined range of values, wherein the processor is arranged to select the first range of energy levels from a first range of energy level values and to select the second range of energy levels from a second range of energy level values, wherein the processor is arranged to calculate the first decomposed image in part by selecting a first decomposition parameter from the plurality of decomposition parameters depending on the value of the first range of energy levels and using the first decomposition parameter to calculate the first decomposed image, and wherein the processor is arranged to calculate the second decomposed image in part by selecting a second decomposition parameter from the plurality of decomposition parameters depending on the value of the second range of energy levels and using the second decomposition parameter to calculate the second decomposed image.

24. The apparatus of claim 1, wherein said processor is arranged to calculate the contrast adjusted image according to the equation:

$$I_{HS} = I_s^{\frac{w_b}{w_b-w_s}} LPF\left(I_b^{\frac{-w_s}{w_b-w_s}}\right)$$

wherein $I_s$ represents the soft structure image, $I_b$ represents the hard structure image, $w_s$ represents the second selected decomposition parameter, $w_b$ represents the first selected decomposition parameter, and LPF represents a low pass filter function.

25. The apparatus of claim 24, wherein said processor is arranged to calculate the contrast adjusted image according to the expression:

$$I_s^{\frac{w_b}{w_b-w_s}} LPF\left(I_b^{\frac{-w_s}{w_b-w_s}}\right),$$

wherein $I_s$ represents the soft structure image, $I_b$ represents the hard structure image, $w_s$ represents the second selected decomposition parameter, $w_b$ represents the first selected decomposition parameter, and LPF represents a low pass filter function.

26. The apparatus of claim 25, wherein the low pass filter function comprises a boxcar filter function.

* * * * *